United States Patent [19]

Freitag et al.

[11] 4,322,373

[45] Mar. 30, 1982

[54] PROCESS FOR THE PREPARATION OF AROMATIC DICARBOXYLIC ACID DICHLORIDES

[75] Inventors: Dieter Freitag, Krefeld, Fed. Rep. of Germany; Manfred Schmidt, New Martinsville, W. Va.

[73] Assignee: Bayer Aktiengesellschaft, Leverkusen, Fed. Rep. of Germany

[21] Appl. No.: 164,342

[22] Filed: Jun. 30, 1980

[30] Foreign Application Priority Data

Jul. 3, 1979 [DE]  Fed. Rep. of Germany ....... 2926789

[51] Int. Cl.³ ............................................. C07C 51/60
[52] U.S. Cl. .................................. 260/544 K; 252/426
[58] Field of Search ..................................... 260/544 K

[56] References Cited

U.S. PATENT DOCUMENTS 3,810,940  5/1974  Hauser ........................... 260/544 K

*Primary Examiner*—Natalie Trousof
*Assistant Examiner*—L. Hendriksen
*Attorney, Agent, or Firm*—Connolly and Hutz

[57] ABSTRACT

A one-stage process for the preparation of pure aromatic dicarboxylic acid dichlorides by reacting an aromatic dicarboxylic acid or an aromatic dicarboxylic acid mixture with phosgene, optionally, in a solvent or diluent, with phosphine imines, phosphorimidates or mixtures thereof as catalysts.

4 Claims, No Drawings

PROCESS FOR THE PREPARATION OF AROMATIC DICARBOXYLIC ACID DICHLORIDES

This invention relates to a one-stage process for the preparation of high purity polycondensable aromatic dicarboxylic acid dichlorides.

The production of aliphatic and aromatic acid chlorides by the reaction of a carboxylic acid with phosgene has been described in U.S. Pat. Nos. 3,184,506; 3,544,626; 3,544,627 and 3,547,960 and in German Offenlegungsschrift Nos. 2,400,007 and 2,321,122. The reaction products obtained from these processes are dark coloured carboxylic acid chlorides which are from 96 to 99% pure. Aromatic dicarboxylic acid dichlorides having such a low degree of purity cannot be used directly in the diphasic interface polycondensation process for the production of high molecular weight polycondensates, such as aromatic polyamides or aromatic polyesters. The presence therein of unreacted or only semi-reacted dicarboxylic acids interface with polycondensation, causes unwanted chain breakage and results in polymers containing carboxyl end groups. The aromatic dicarboxylic acid dichlorides obtained are dark in colour due to the impurities and have an undesirable carbamic acid chloride content resulting from the reaction thereof with catalysts (see Chem. Ref. 1973, Vol. 73, No. 1, page 77 or Angewandte Chemie (1974), Year 1962, No. 21, page 864).

If colourless dicarboxylic acid dichlorides are to be obtained, the crude products must be purified by recrystallisation or distillation. This requires additional effort and reduces the yield and, in the case of aromatic dicarboxylic acid dichlorides, there is the risk of spontaneous decomposition.

The present invention relates to a one-stage process for the preparation of pure aromatic dicarboxylic acid dichlorides by the reaction of an aromatic dicarboxylic acid with phosgene in the presence of a catalyst and optionally in a solvent and/or diluent, characterised in that the catalysts used are phosphine imines or phosphorimidates or mixtures thereof. The aromatic dicarboxylic acid dichlorides obtained are virtually colourless and apart from the catalysts put into the process contain 0.1% or less of impurities so that they may be directly used for the preparation of colourless, high molecular weight polycondensates without being first purified.

The phosphine imines or phosphorimidates or mixtures thereof used as catalysts according to the present invention do not interfere with the subsequent processes, such as the preparation of aromatic polyesters. The catalysts are separated from the organic polymer solution by the aqueous alkaline phase when the product is subsequently washed by the two-phase interface method after polycondensation.

Suitable catalysts according to the present invention include phosphine imines corresponding to general formula (I) and phosphorimidates corresponding to general formula (II):

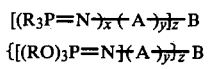  (I)
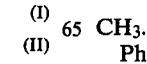  (II)

wherein when $z=1$, R and

B represent $C_1$–$C_8$ alkyl, $C_6$–$C_{10}$ aryl, $C_7$–$C_{20}$ alkylaryl or arylalkyl;
$y=0$ and $x=1$ or
$y=1$ and $x=1$ when A represents $$-CO-, \quad -\underset{\underset{O}{\|}}{C}-O-$$

or $-SO_2-$; or
$y=1$ and $x=2$ when A represents

and, when $z=2$ or 3, A, R, x, and y are as defined above, but B represents $C_6$–$C_{10}$ aryl or $C_7$–$C_{20}$ alkylaryl.

Phosphine imines or phosphorimidates corresponding to general formulae (III) and (IV) are also suitable catalysts according to the present invention:

(III)          (IV)

wherein R is as defined above;
M represents $CH_3$ or $C_6H_5$;
and $n,m = 1,2$ or 3,
and $n+m=4$.

The following are examples of individual compounds which are suitable:

$R'_3P=N-D$, $R'_3P=N-\underset{\underset{O}{\|}}{C}-R''$,

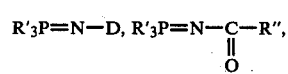, $R'_3P=N-SO_2R'''$ or

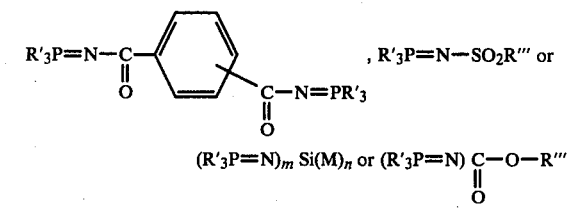

wherein
R' represents $CH_3$, $C_6H_5$, $C_2H_5O$, $CH_3O$ or $C_6H_5O$;
D represents $CH_3$, $C_6H_5$,

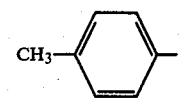

or cyclohexyl;
R'' represents $CH_3$, $C_6H_5$ or $C_{10}H_7$; and
R''' represents $C_6H_{13}$, $C_4F_9$, $C_6H_5$,

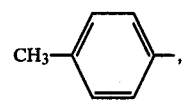

$CH_3$.

Phosphine imines corresponding to general formula (I) or (III) and phosphorimidates corresponding to general formula (II) or (IV) which are suitable catalysts according to the present invention may be prepared, for example, by the reaction of tertiary phosphines or of phosphites with the corresponding azides accompanied by the elimination of nitrogen in accordance with the following reaction scheme (see Kosolapoff, Maier "Organic Phosphorous Compounds", Vol. 3, pages 71–73 and 127–153, and Vol. 6, pages 611–612):

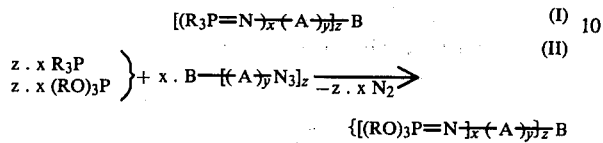

The following individual compounds are particularly suitable:

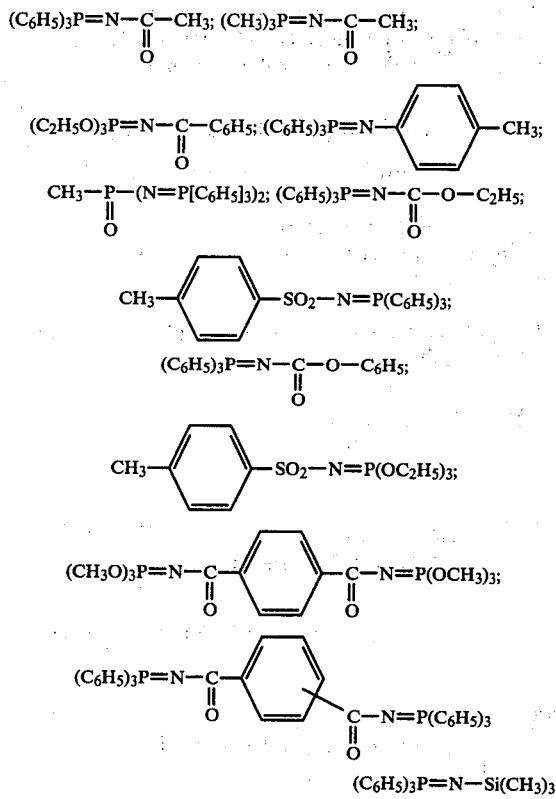

According to the present invention, the phosphine imines or phosphorimidates or mixtures thereof are used in quantities of from 0.1 to 3.0%, by weight, preferably from 0.2 to 1.5%, by weight, based on the aromatic dicarboxylic acids used.

Aromatic dicarboxylic acids correspond to the following general formulae:

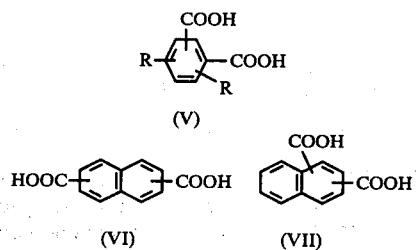

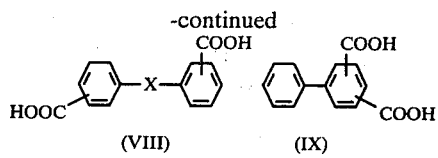

wherein
R represents H, $C_1$–$C_4$ alkyl or halogen (preferably chlorine or bromine);
X represents a single bond, —O—, —S—, —$CH_2$,

or $C_5$–$C_7$ cycloalkylene.
Mixtures may also be used.

The following are examples: phthalic acid, isophthalic acid, terephthalic acid, mixtures of iso- and tere-phthalic acid, diphenic acid and 1,4-naphthalene dicarboxylic acid.

The solvent or diluent used is preferably the aromatic dicarboxylic acid dichloride or mixture of aromatic dicarboxylic acid dichlorides formed during the reaction. Inert diluents, such as aliphatic or aromatic hydrocarbons, halogen-substituted aromatic hydrocarbons, halogen-substituted aliphatic hydrocarbons or saturated aliphatic ethers, may also be added. The reaction temperature is generally from 70° to 180° C., preferably from 100° to 160° C.

The molar ratio of aromatic dicarboxylic acid to phosgene is preferably from 1:2 to 1:2.5, i.e. is advisable to use a slight excess of phosgene to replace the losses resulting from the expulsion of $CO_2$ and HCl gas from the reaction mixture during phosgenation.

The process according to the present invention may be carried out batch-wise or continuously. In one continuous embodiment, a solution of aromatic dicarboxylic dicarboxylic acid dichloride and catalyst flows down a reaction tube counter to an upward stream of phosgene gas, and the aromatic dicarboxylic acid dichloride and catalyst are removed at the bottom of the reaction tube.

In a batch-wise embodiment, aromatic dicarboxylic acid, aromatic dicarboxylic acid dichloride and catalyst are introduced into a reaction vessel at normal pressure. The reaction mixture is then heated to from 140° to 160° C., with stirring, the aromatic dicarboxylic acid partly or completely dissolving under these conditions. From 2 to 2.5 mol of gaseous phosgene per mol of aromatic dicarboxylic acid are introduced at this temperature.

The residue obtained after removal of excess phosgene, HCl and $CO_2$ gas by brief application of a vacuum contains ≧99.9% of aromatic dicarboxylic acid dichloride in addition to the quantity of catalyst used and may be converted into high molecular weight colourless polycondensates without further purification.

EXAMPLE 1

203 g (1 mol) of isophthalic acid dichloride, 166 g of isophthalic acid (1 mol) and 0.8 g of:

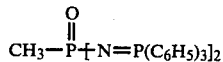

are heated to 148° C. in a round-bottomed flask which is equipped with thermometer and stirrer and with a condenser which is maintained at −20° C. by means of cooling brine. Phosgene is introduced at from 148° to 157° C., with stirring, and the mixture is refluxed until the temperature of the reaction mixture falls to 146° C.

After cooling of the reaction mixture to 120° C., a water jet vacuum is applied to remove excess phosgene, as well as any HCl and $CO_2$ gas dissolved in the reaction mixture.

Yield: 406.5 g of a colourless residue consisting of 0.8 g of the phosphine imine catalyst put into the process and 405.7 g of a 100% isophthalic acid dichloride (determined by titration).

EXAMPLE 2

101.5 g (0.5 mol) of isophthalic acid dichloride, 101.5 g (0.5 mol) of terephthalic acid dichloride, 83 g (0.5 mol) of isophthalic acid, 83 g (0.5 mol) of terephthalic acid and 0.8 g of:

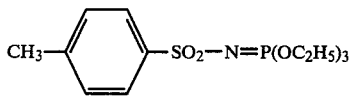

are reacted with phosgene as described in Example 1.

Yield: 406.8 g of a colourless residue consisting of 0.8 g of the phosphorimidate catalyst put into the process and 406 g of a mixture of 100% isophthalic and terephthalic acid dichloride (determined titrimetrically).

EXAMPLE 3

101.5 g (0.5 mole) of isophthalic acid dichloride, 101.5 g (0.5 mol) of terephthalic acid dichloride, 83 g (0.5 mol) of isophthalic acid, 83 g (0.5 mol) of terephthalic acid and 0.8 g of:

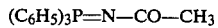

are reacted with phosgene as described in Example 1.

Yield: 406 g of 99.9% isophthalic and terephthalic acid dichloride and 0.8 g of the phosphine imine catalyst put into the process.

EXAMPLE 4

101.5 g (0.5 mol) of isophthalic acid dichloride, 101.5 g (0.5 mol) of terephthalic acid dichloride, 83 g (0.5 mol) of isophthalic acid, 83 g (0.5 mol) of terephthalic acid and 0.3 g of catalyst corresponding to the formula:

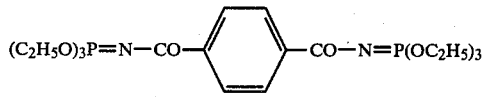

are reacted with phosgene as described in Example 1.

Yield: 406 g of an almost colourless residue of 0.3 g of catalyst and 405.7 g of a mixture of 100% isophthalic and terephthalic acid dichloride (determined titrimetrically).

We claim:

1. A process for preparing an aromatic dicarboxylic acid dichloride which comprises reacting an aromatic dicarboxylic acid with phosgene in the presence of a catalytic amount of at least one phosphine imine or phosphoramidate, said aromatic dicarboxylic acid being selected from the group consisting of

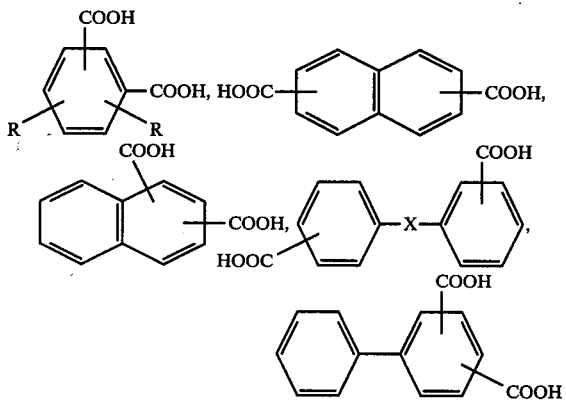

and mixtures thereof wherein R is hydrogen, alkyl having 1 to 4 carbon atoms or halogen and —X— is a single bond, —O—, —S—, —CH$_2$—,

or cycloalkylene having 5 to 7 carbon atoms.

2. A process of claim 1 wherein said reaction is carried out in the presence of a reaction inert diluent.

3. A process of claim 1 wherein said phosphine imine is of the formula

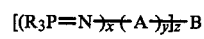

and said phosphorimidate is of the formula

wherein when z equals 1, R and B are $C_1$–$C_8$ alkyl, $C_6$–$C_{10}$ aryl, $C_7$–$C_{20}$ alkaryl or $C_7$–$C_{20}$ aralkyl; y is 0 and x is 1 or y is 1, x is 1 and A is —CO—,

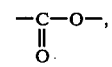

or —SO$_2$— or y is 1, x is 2 and

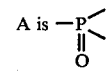

or when z is 2 or 3, A, R, x and y are each as aforesaid and B is $C_6$–$C_{10}$ aryl or $C_7$–$C_{20}$ alkaryl.

4. A process of claim 1 wherein said phosphine imine is of the formula

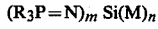

and said phosphorimidate is of the formula

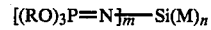

wherein R is $C_1$–$C_8$ alkyl, $C_6$–$C_{10}$ aryl, $C_7$–$C_{20}$ alkaryl or $C_7$–$C_{20}$ aralkyl, M is $CH_3$ or $C_6H_5$, n and m are each 1, 2 or 3 and n+m is 4.

* * * * *